United States Patent [19]

Melcher et al.

[11] Patent Number: 5,221,477
[45] Date of Patent: Jun. 22, 1993

[54] APPARATUS AND METHOD FOR REVERSED PERMEATION MEMBRANE EXTRACTION OF COMPOUNDS FROM SAMPLE SOLUTIONS

[75] Inventors: Richard G. Melcher; Paul J. O'Connor, both of Midland, Mich.

[73] Assignee: The Dow Chemical Company, Midland, Mich.

[21] Appl. No.: 893,874

[22] Filed: Jun. 5, 1992

[51] Int. Cl.⁵ .................. B01D 11/00; B01D 29/13
[52] U.S. Cl. ........................... 210/634; 210/650; 210/656; 210/198.2; 210/490; 210/500.23; 210/323.2; 210/506; 436/161
[58] Field of Search ............ 210/651, 652, 490, 635, 210/638, 198.2, 259, 634, 500.27, 506, 500.23, 323.2, 656; 436/161; 55/386

[56] References Cited

U.S. PATENT DOCUMENTS

| | | | |
|---|---|---|---|
| 3,967,928 | 7/1976 | Schmidt et al. | 423/449 |
| 4,094,669 | 6/1978 | Balko et al. | 423/562 |
| 4,525,278 | 6/1985 | Frost, III | 210/638 |
| 4,529,521 | 7/1985 | Cortes et al. | 210/635 |
| 4,738,781 | 4/1988 | Word et al. | 210/637 |
| 4,775,476 | 10/1988 | Melcher et al. | 210/637 |
| 4,819,478 | 4/1989 | Melcher | 210/635 |
| 4,891,137 | 6/1990 | Nohl et al. | 210/656 |
| 4,913,821 | 4/1990 | Melcher et al. | 210/635 |
| 4,957,620 | 9/1990 | Cussler | 210/500.23 |
| 4,962,042 | 10/1990 | Morabito et al. | 55/386 |
| 4,976,869 | 12/1990 | Taylor | 210/500.23 |
| 4,999,105 | 3/1991 | Melcher et al. | 210/198.2 |
| 5,079,168 | 1/1992 | Amiot | 210/321.69 |

FOREIGN PATENT DOCUMENTS

25128A1 12/1987 Fed. Rep. of Germany.

OTHER PUBLICATIONS

Direct Gas Chromatographic Analysis of Aqueous samples at the Part-per-Billion and Part-per-Trillion Levels, Zlatkis et al.—Oct. 1983, *Analytical Chem.* vol. 55.
Uncoated Capillary Columns and their Thermal Desorption, Zlatkis et al.—Jul. 1990 *Chromatographia*, vol. 29, No. 11/12.
Rapid Analysis of Trace Organics in Aqueous Solutions by Enrichment in Uncoated Capillary Columns, Zlatkis et al.—Aug. 1990, *Chromatographia*, vol. 30.
Concentration of Organics from Aqueous Solutions Using Uncoated Capillary Columns Zlatkis et al.—Nov. 15, 1990, *Analytical Chemistry*, vol. 62.
Environmental Protection Agency Guidelines, *Federal Register*, vol. 44, Dec. 3, 1979.
Membrane/Gas Chromatographic System for Automated Extraction and Determination of Trace Organics in Aqueous Samples, Melcher, et al. *Analytical Chemistry*, Oct. 15, 1990.

Primary Examiner—Robert A. Dawson
Assistant Examiner—Ana M. Fortuna
Attorney, Agent, or Firm—Ronald J. Snyder; Timothy S. Stevens

[57] ABSTRACT

A reversed permeation membrane assembly and method for collecting one or more compounds of interest from a sample solution. The membrane assembly includes a semi-permeable membrane of predetermined thickness and length, and having inner and outer surfaces. The membrane is attached adjacent its outer surface to a substantially rigid membrane support, and a non-porous barrier contacts the outer surface of the membrane to prevent permeation of compounds beyond the outer surface in use. In a preferred embodiment, the semi-permeable membrane assumes a substantially tubular conformation through which sample solution may be passed. The membrane support also preferably features a tubular conformation within which the semi-permeable membrane is mounted. Because of its unique structure and improved efficiency, the assembly of the present invention may be incorporated for in-line use with liquid and gas chromatography devices and GC/MS units. In some applications, the extractant can even be flowed through the membrane cell to collect analytes and directly to an LC column for analysis in a substantially non-stop manner.

17 Claims, 9 Drawing Sheets

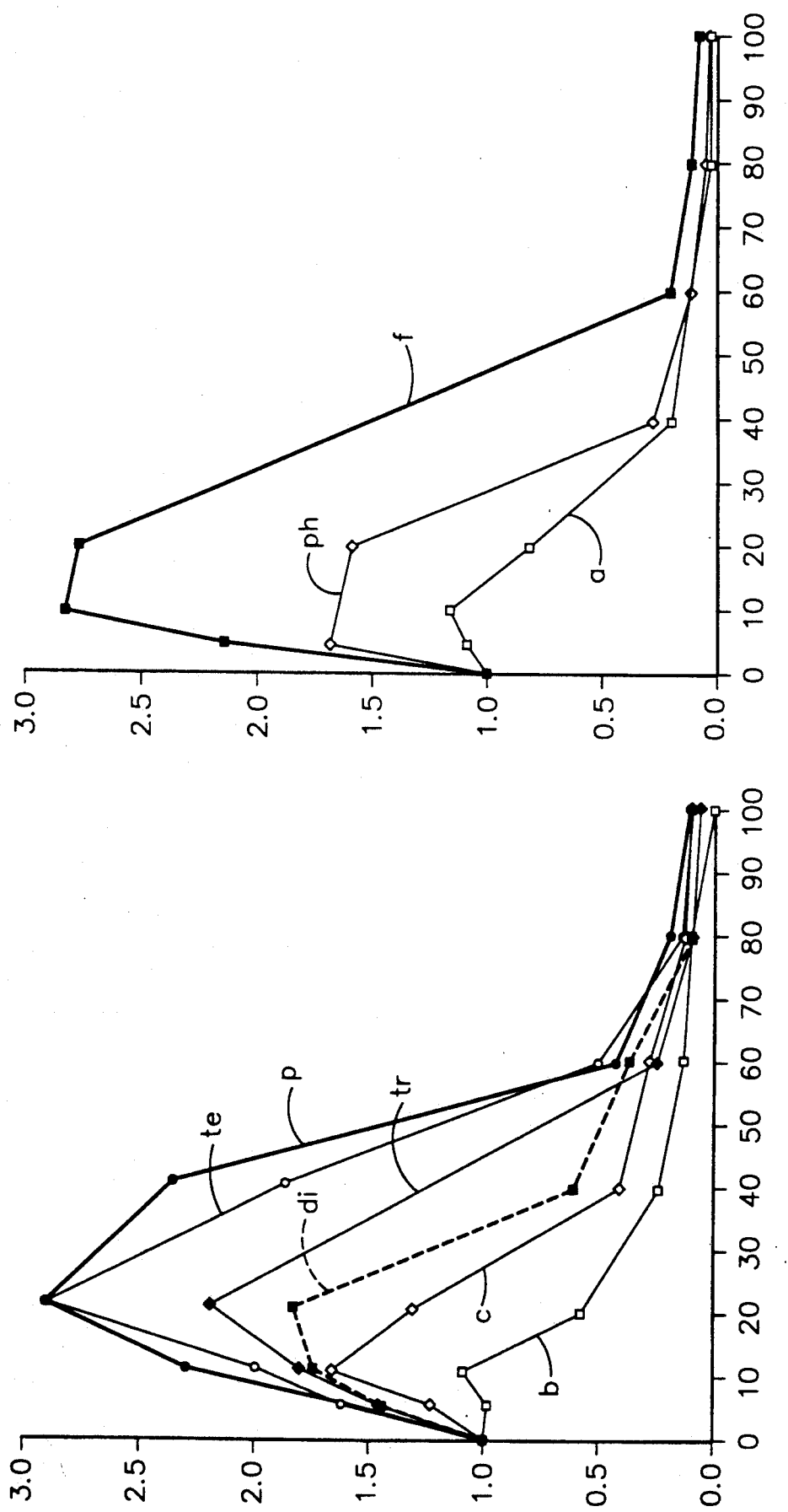

APPARATUS AND METHOD FOR REVERSED PERMEATION MEMBRANE EXTRACTION OF COMPOUNDS FROM SAMPLE SOLUTIONS

TECHNICAL FIELD

This invention relates to methods and devices for analyzing waste-water and other solutions for trace organic compounds and the like, and, more particularly to a reversed permeation membrane (RPM) extraction system for concentration and subsequent determination of trace organics in sample solutions. The subject reversed permeation membrane arrangement enables a much simplified structure and process for selective collection of compounds of interest with reduced lower limits of detection and easy adaptability to a wide variety of standard separation and analyzing equipment.

BACKGROUND ART

With the ever increasing environmental consciousness of the world, the presence of trace organics in water, waste-water, and other effluents has also become increasingly important. Because many of these substances have toxic, carcinogenic, mutagenic and teratogenic properties, their presence, and particularly their concentrations, have increasingly become the focus of both environmental and health scrutiny. Particularly, the allowable concentration of a wide variety of potentially toxic compounds in waste-water is extremely low, as many have significant adverse effects and toxic activity, even when present in only trace levels of concentration (e.g., several parts per billion, or parts per trillion).

Continuing studies have been directed toward testing for, controlling, and determining permissible levels of a wide range of potentially toxic compounds, and much research has consequently gone into developing improved devices and procedures for testing for the presence of these various compounds. For example, the Environmental Protection Agency has adopted certain methods for the analysis of what have been named "priority pollutants" (as set forth in the Federal Register, Vol. 44, pp. 69,464 et seq. (1979)). Among these adopted methods are chromatographic techniques, combined gas chromatography and mass spectrometry techniques (GC/MS), and others. In addition to each of the various classes of compounds having their own specific analytical procedure for sampling, storing, collecting, and analyzing, it is widely understood in the industry that the EPA methods of analysis are labor intensive, equipment intensive, time consuming, and, as a result, costly. It is not unusual for an analysis of waste-water to take two days or more for result to be obtained. Many of these processes also require the collection of a relatively large sample volume (e.g., 1 liter), utilize relatively extensive amounts of laboratory glassware, tubing, and the like, require a relatively large volume of solvent for extraction and cleaning of the glassware and apparatus, and/or require significant energy input to evaporate the solvent and concentrate the sample compounds.

In general, compounds of interest have been extracted from waste-water for identification and quantification by passing a relatively large volume of the waste-water through a bed of granulated charcoal. U.S. Pat. No. 3,967,928 (Schmidt et al.) discusses a method of this type, wherein molecules are adsorbed on activated carbon product, followed by desorption. The compounds of interest are generally aborbed into the charcoal, after which a volume of extract (e.g., chloroform or the like) is passed through the bed of charcoal to release the adsorbed compounds. The extractant can be in the form of a solvent or a gas, and is generally chosen to release the compounds of interest from the charcoal bed. Thereafter, the extractant is evaporated to facilitate the assay of the concentrations and characteristics of the various compounds via a gas chromatograph (GC) device. While this particular procedure is widely utilized, because waste-water often contains particulate matter, the granular adsorbent can easily become plugged or otherwise clogged, thereby interfering with the reliability and efficiency of results obtained.

Other devices and methods for recovering compounds from waste solutions include the incorporation of a two-sided membrane, such as described in U.S. Pat. Nos. 4,525,278 (which issued to A. Frost) and 4,738,781 (which issued to W. Word et al.). Particularly, these references described ultrafiltration devices wherein waste-water or the like is fed through a tubular membrane of a non-cellulosic polymer through which compounds of interest permeate for removal through a separate output. Emulsified oils and suspended particles cannot pass through the membrane, and are removed as concentrated retente. The micro-porous membrane includes an exterior support tube which must also be porous in nature, such that it will have a low resistance to the permeating flow of the compounds of interest. Other references describing the use of two sided membranes for extraction of compounds of interest include U.S. Pat. Nos. 4,775,476 (Melcher et al.) and 4,819,478 (Melcher). While a two-sided membrane arrangement can be useful in certain circumstances, it is severely limited by the size and type of compounds which can permeate therethrough, must be isolated from pressure, and/or requires a porous supporting structure which must also be designed to allow penetration, and often requires relatively lengthy concentration times to allow for the permeation of the compounds completely through the membrane. Additionally, cleanup procedures are correspondingly difficult and time consuming, and potential carryover from previous test cycles can seriously undermine reliability of results.

Other methods for concentration of organics from aqueous solutions include the passage of the sample through an uncoated plastic or metal capillary tubing. For example, the procedures reported by Zlatkis et al. incorporated the use of relatively long capillaries (e.g., 50-100 feet) through which aqueous solutions were passed. The organic compounds would be retained in the tubing walls while the balance of the waste-water eluted from the capillary tubes. The concentrated organics were then desorbed from the capillary using an organic solvent, generally pushed through the capillary by nitrogen gas or the like. The desorbed solution was then analyzed by gas chromatography. Zlatkis et al. specifically set forth various problems with prior extraction techniques and devices, such as the charcoal filters discussed above. However, it was also reported that the effort to desorb the trapped organics were not satisfactory, and the use of metal capillaries was seriously questioned. Other methods for desorbing the organics, such as heating the matrix and/or utilizing a membrane dryer arrangement, were attempted to help remove the relatively large volumes of retained water required. Moreover, because long capillaries were needed, the cost, space and equipment requirements, and time for collection and analysis were clear negatives for the applicability and efficiency of these systems.

Consequently, there has heretofore not been available in the industry a relatively simple device and process for the extraction of particular compounds from sample solutions in a relatively reliable, efficient, and timely manner. Additionally, due to the permeable nature of two-sided membranes and their required porous supporting structures, as well as the cumbersome length of the capillary tubes utilized for GC analysis by Zlatkis et al., the methods and apparatuses previously available have not been easily adaptable to a variety of separation and assaying arrangements. A device and process having the higher sensitivity required for trace component analysis, while enabling smaller sample sizes and compatibility with water as both the sample and extractant carrier system and which can be used on-line with liquid chromatography and/or other separation/analyzing devices was needed. Moreover, the devices previously available were generally not easily used in conjunction with techniques requiring elevated temperatures and/or pressures.

DISCLOSURE OF THE INVENTION

It is an object of this invention to obviate the above-described problems and shortcomings of the devices and methods for extraction of compounds from sample solutions heretofore available in the industry.

It is another object of the present invention to provide an improved method and apparatus for use in extracting compounds of interest from sample solutions having faster sample times and higher sensitivity.

It is yet another object of the present invention to provide an improved device and method for extraction of compounds from solutions which is relatively simple in structure and function, and which can be easily adapted for on-line use with a variety of available separation and/or analyzing devices such as flow injection analysis, gas chromatography, gas chromatography/mass spectrometer, high-performance liquid chromatography, and the like.

It is also an object of the present invention to provide an apparatus and method for reversed permeation membrane extraction of compounds from sample solutions which enables selective analyte collection from smaller sample volumes, and which features shorter cycle times and improved carryover prevention.

It is yet another object of the present invention to provide a device and method for reversed permeation membrane extraction which enables adjustment in the dilution or concentration of compounds of interest, and facilitates remote sampling of solutions, yet can be utilized in conjunction with analyzing systems requiring elevated temperatures and/or pressures.

In accordance with one aspect of the present invention, there is provided a reversed permeation membrane assembly for collecting one or more compounds of interest from a sample solution. The membrane assembly includes a semi-permeable membrane of predetermined thickness and length, and having inner and outer surfaces. The membrane is attached adjacent its outer surface to a substantially rigid membrane support, and a non-porous barrier contacts the outer surface of the membrane to prevent permeation of compounds beyond the outer surface in use. In a preferred embodiment, the semi-permeable membrane assumes a substantially tubular conformation through which sample solution may be passed. The membrane support also preferably features a tubular conformation within which the semi-permeable membrane is mounted.

Because the membrane assembly of the present invention can be connected on-line with various analytical devices such as gas and liquid chromatographs, it is also preferred that peripheral seals be provided between the membrane and its tubular support adjacent the oppositely disposed ends of the assembly. The non-porous barrier can conveniently be provided in the form of a non-porous inner surface of the rigid membrane support, which can be provided in the form of an inner coating or, more simply, by providing the membrane support of non-porous material.

The present invention further pertains to a method of collecting one or more compounds of interest from a sample solution wherein a volume of the solution is passed in contact with the inner surface of the membrane so that compounds of interest permeate thereinto. Thereafter, an extractant solution is passed in contact with the inner surface of the membrane to extract one or more permeated compound from the membrane, with assay of the extracted compound being thereafter completed. In a preferred embodiment, the method further includes a step of flushing the sample solution from the membrane cell after one or more compound of interest has permeated into the membrane. As mentioned above, in a preferred set-up, the step of assaying the collected compound may be completed on-line by liquid or gas chromatography, or other analytical procedures.

BRIEF DESCRIPTION OF THE DRAWINGS

While the specification concludes with claims particularly pointing out and distinctly claiming the present invention, it is believed the same will be better understood from the following description taken in conjunction with accompanying drawings in which:

FIGS. 10A and 10B are graphs illustrating test results comparing the effects of organic solvents on RPM extraction according to the invention, wherein analyte signal is plotted against percent acetonitrile in the water based solvent; and FIGS. 11A and 11B are graphs illustrating test results showing signal enhancement by solvent solutions, wherein FIG. 11A shows signal intensities for pentachlorobenzene against various Hildebrand solubility parameter (HSP) of the sample solution, and FIG. 11B shows a similar plot for fluoranthene.

DETAILED DESCRIPTION OF THE INVENTION

Figure 1:
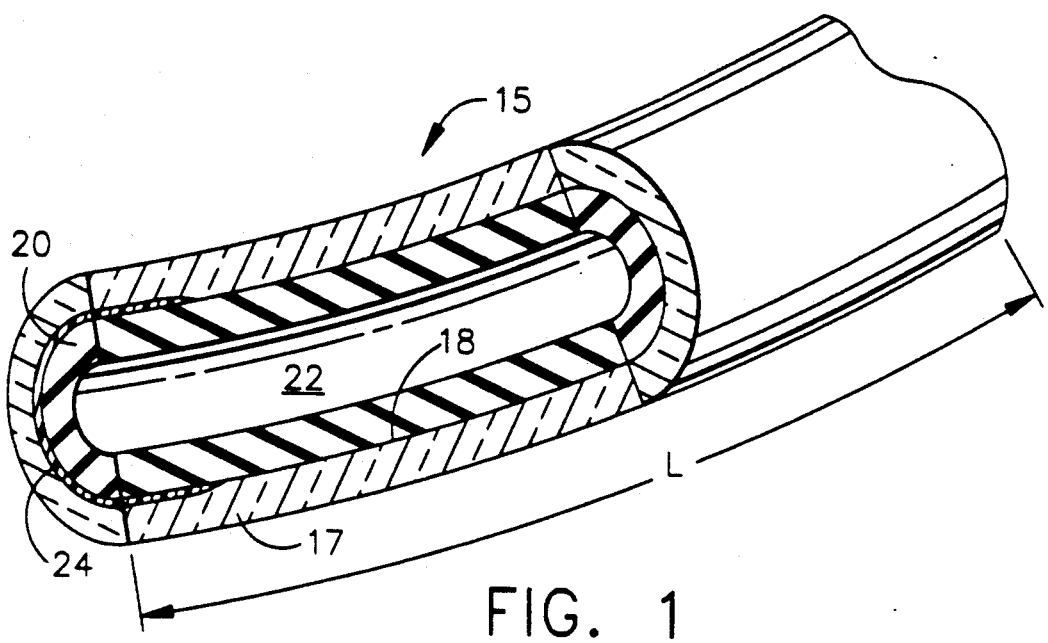
FIG. 1 is an enlarged, partially broken-out perspective view of a portion of a reversed permeation membrane cell made in accordance with the present invention.

Referring now to the drawings in detail, wherein like numerals indicate like elements among the various views, the apparatus and method of the subject invention for analyzing trace organics with low solvent and sample requirements will be described. Particularly, the present invention pertains to an apparatus and method for improved extraction of compounds from sample solutions, which incorporates a "one-sided" membrane 15 as illustrated in FIG. 1. Membrane 15 further comprises a membrane support 17 having at least one nonporous face 18 on which a semi-permeable membrane 20 will be supported.

As illustrated in FIG. 1, membrane support 17 can preferably comprise a length (L) of teflon tubing having a predetermined inside diameter (e.g., approximately 0.0625 inches or 1.58 mm). As will be described below, while the semi-permeable membrane can be provided of varying thicknesses and materials, depending upon the particular application and compounds to be analyzed, it may preferably comprise a silicone rubber (e.g., Silastic as available from Dow Corning) having predetermined inside and outside diameters for support within membrane support 17. The supported membrane 15 will provide a predetermined flow channel 22 through which sample solution and solvent will be passed, as described below.

It is also contemplated that a particular reversed permeation membrane cell 15 will further preferably comprise membrane/support seals 24 adjacent the opposite ends of the longitudinal length L thereof. Because sample solutions such as waste-water and the like will be flowed through membrane cell 15, and may often be subjected to elevated pressures and/or temperatures, a reliable connection and seal between semi-permeable membrane 20 and its support 17 will be needed at least adjacent the opposite ends of the membrane cell 15. The manner in which seals 24 are provided in any particular membrane/support arrangement may vary depending upon the specific materials utilized for membrane support 17 and the selectively permeable membrane 20. For example, when membrane 20 is provided of a silicone rubber material, it may be preferred to utilize silicone sealant at either end to provide a reliable and compatible seal.

While it is contemplated that the membrane cell 15 can be assembled by inserting a semi-permeable membrane 20 into a corresponding membrane support 17 and sealing the opposite ends therewithin, the manner of creating membrane cell 15 is not critical to the present invention. For example, for some combinations of materials, membrane support 17 and membrane 20 may be simultaneously formed, such as by co-extrusion or the like. Membrane 20 may alternately be coated onto support 17, or formed by the chemical bonding of appropriate materials to support 17.

Figure 2:
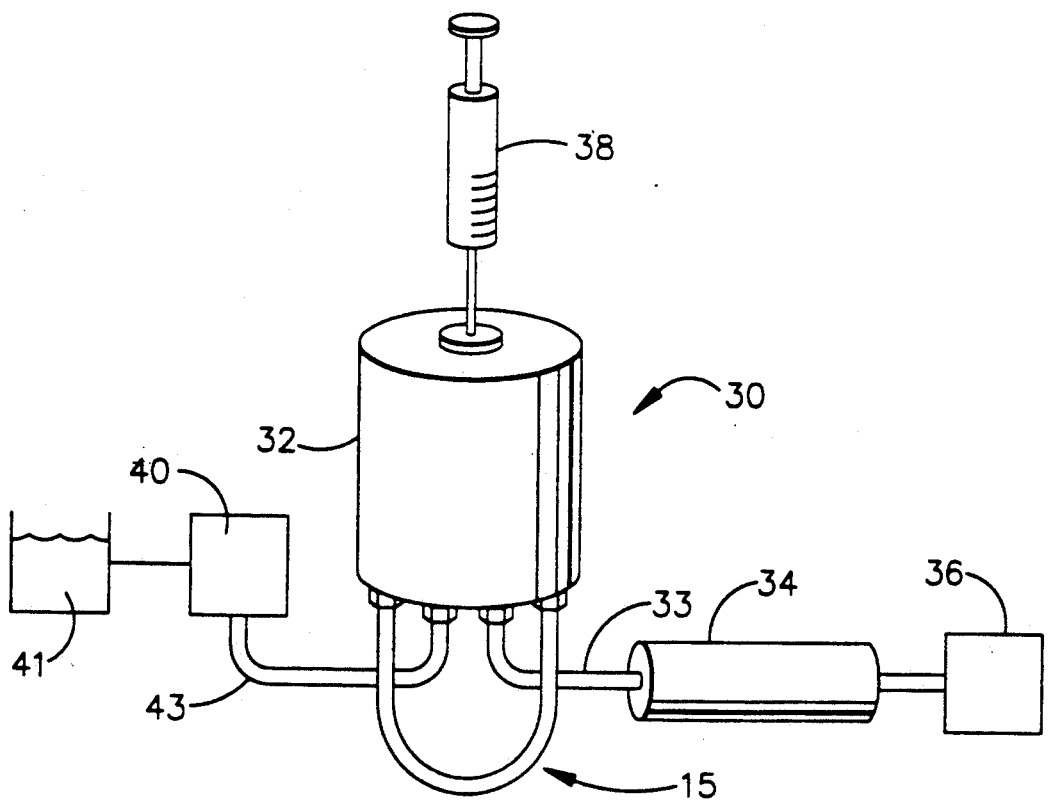
FIG. 2 is a schematic view of an apparatus for reversed permeation membrane extraction made in accordance with the present invention, and illustrated in an experimental set-up for use in conjunction with a liquid chromatography analytical arrangement.

FIG. 2 illustrates an analytical system assembly 30 comprising a reversed permeation membrane (RPM) extraction cell 15 as discussed above attached to a liquid chromatography valve 32 (e.g., an LC valve 7120 as available from Rheodyne of Berkeley, Calif.) for use in conjunction with an LC flow cell column 34 (e.g., a Brownlee RPC$_{18}$ 5 u OD-032 guard) and detector 36 (e.g., a UV, 285 mm, range 0.01, Att64). As also illustrated, assembly 30 might preferably comprise an injection syringe 38 coupled to one input of valve 32, and a liquid chromatograph eluent pump 40 connected to a source of LC eluent 41 (e.g., 35% acetonitrile/65% 0.01M phosphoric acid) to provide extractant solvent to the analytical system via supply tube 43 and valve 32.

Experimental tests were run on an analytical system assembly essentially as described above, whereby sample solution was filled into RPM cell 15 and held therewithin for various predetermined time periods (i.e., 0.5, 1.0, 2.0, and 4.0 minutes) before being flushed with water, a flushing solution, or gas (e.g., air, nitrogen or the like). As the sample solution is passed through cell 15, compounds of interest in the sample solution (e.g., priority pollutants such as chlorophenols, benzene, chlorobenzene and polycyclic aromatic hydrocarbons) permeate into semi-permeable membrane 20.

Figure 3:
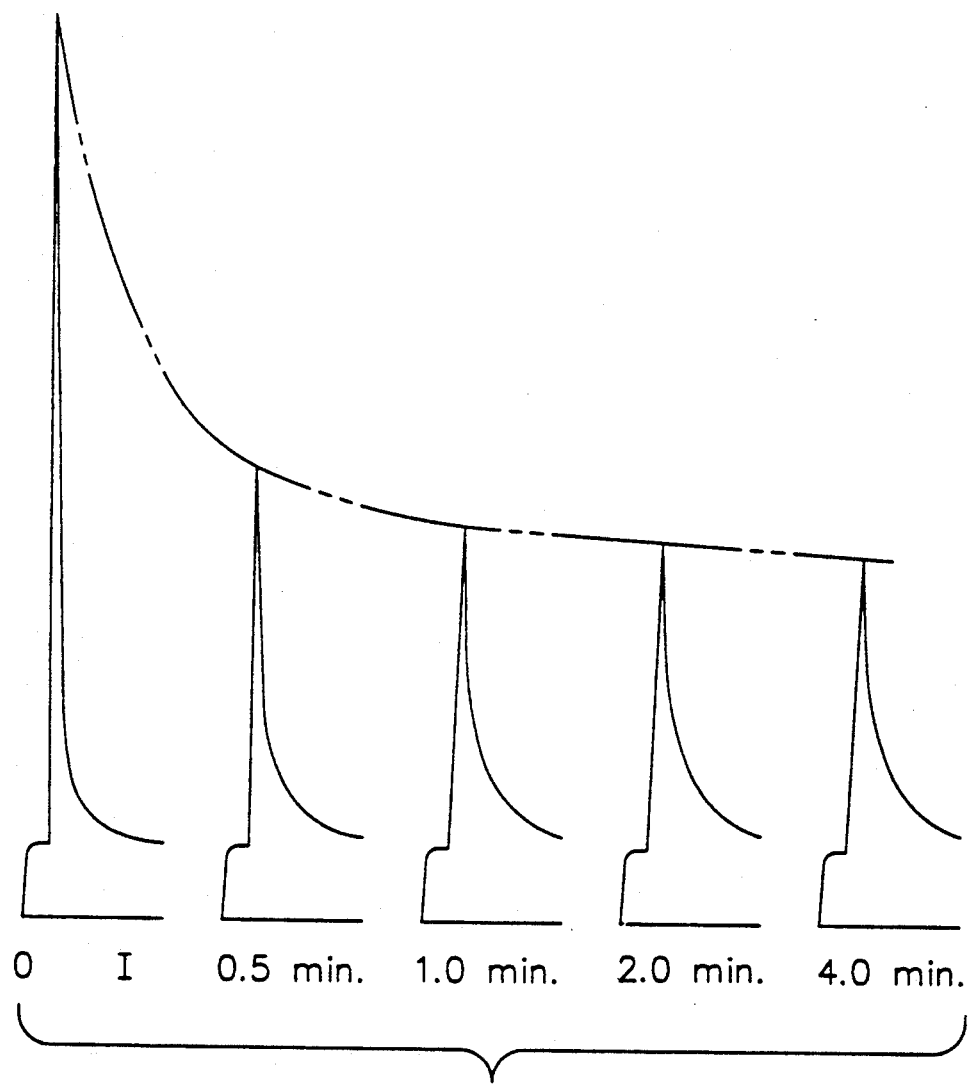
FIG. 3 illustrates a series of chromatograms of extraction profiles for 3,5-dichlorophenol obtained at various sampling times from an RPM extraction arrangement of the present invention.

The experimental set-up as shown in FIG. 2 was utilized in various ways to investigate the operational characteristics of the subject RPM cell. One experiment was to determine the extraction of compounds of interest into the membrane and the reversed permeation extraction profile into the extractant eluent flowing through the cell. In this experiment, the LC column was a Brownlee RPC$_{18}$, 5 micron OD-032 guard set-up, and the sample solution was acidified water containing 10 ppm 3, 5-dichlorophenol. The amount of sample loaded into the RPM was 0.2 ml, and the extractant solvent comprised 35% acetonitrile and 65% 0.01M phosphoric acid. Sample was filled into RPM cell 15 and held for various sample extraction times of 0.5, 1.0, 2.0 and 4.0 minutes before being flushed from the system. Thereafter, the extraction eluent was directed through the membrane cell 15 and "injected" into the LC column 34 for detection by detector 36. FIG. 3 graphically illustrates chromatograms showing the recovery profiles of the RPM extraction tests at the respective sample extraction times.

One sample (e.g., shown as peak I on FIG. 3) was directly injected as soon as the RPM was loaded, and no flush was used. As can be appreciated from FIG. 3, for this direct injection, most of the dichlorophenol analyte is still in the aqueous phase. The peaks for extraction times 0.5, 1.0, 2.0 and 4.0 minutes each represent only the amount of compound which has permeated the membrane, since all non-permeated material has been flushed out. Because the analyte can be carried to the detector only as it diffuses back out of the membrane, the peaks indicate the profile of the "desorption" or back diffusion of the analyte. The recovery profiles of the 1, 2 and 4 minute tests are quite similar, indicating that analyte extraction was essentially completed in approximately 1 to 2 minutes. As can be appreciated, because the compounds of interest do not have to diffuse or permeate through the entire width of the membrane wall to a collection side (as was required with the two-sided membranes often utilized heretofore), the present apparatus and method can be quite useful for molecules which have a relatively slow diffusion rate. Moreover, since the semi-permeable membrane 20 of the present invention is effectively completely supported (e.g., via membrane support 17), high pressures and/or temperatures can be utilized in the system, and high pressure LC columns and the like can be connected directly thereto. Moreover, the requirement for a non-porous support member contacting the membrane allows a wider variety of membrane materials to be utilized.

Once the compounds of interest have been allowed to permeate into the membrane, the balance of the sample solution is passed from cell 15 to a waste collection container or the like. Cell 15 is then flushed out with some type of solvent, which may preferably be water, water/methanol, water/ethanol or methanol, to remove all non-permeated compounds, inorganics and particulates. It should also be noted that the flushing solvent can be chosen to further "select" which compounds are concentrated within membrane 20, as the flushing solvent can be utilized to desorb non-desired components from membrane 20 in addition to flushing residual sample matrix from cell 15. An example would be where five compounds readily permeate membrane 20, but only two of the compounds are of particular interest in the testing procedures, or where three of the five compounds are present in much higher relative concentrations. By appropriately choosing the flushing solution, the other three compounds which have permeated into membrane 20 can be selectively removed (or their concentrations reduced) during the flushing cycle.

Once the permeation or concentration step is followed by an appropriate flushing step, an extractant solvent or eluent is used to collect the permeated compounds from the membrane. Again, the mechanism for desorbtion from membrane 20 is reversed permeation of the compounds into the extract solvent. The choice of the extractant solvent adds additional selectivity to the overall extraction process in that different solvent properties (e.g., pH, solubility, polar characteristics, etc.) can be utilized to extract certain compounds to the exclusion of others. As discussed below, the driving force in each step of the process is maintenance of appropriate water partition coefficients between the fluid in flow channel 22 and the membrane interface. By optimizing the various RPM parameters, substantial selectivity in collection and concentration of particular compounds of interest can be achieved. As also indicated from the experimental results, the permeation and extractant times required for relatively efficient concentration and collection procedures is substantially reduced, as is the required collection column lengths. The time, space, capital investment and labor savings which result from these and the other unique features of the present extraction apparatus and method provide a new dimension in trace element analysis and related applications.

Figure 4:
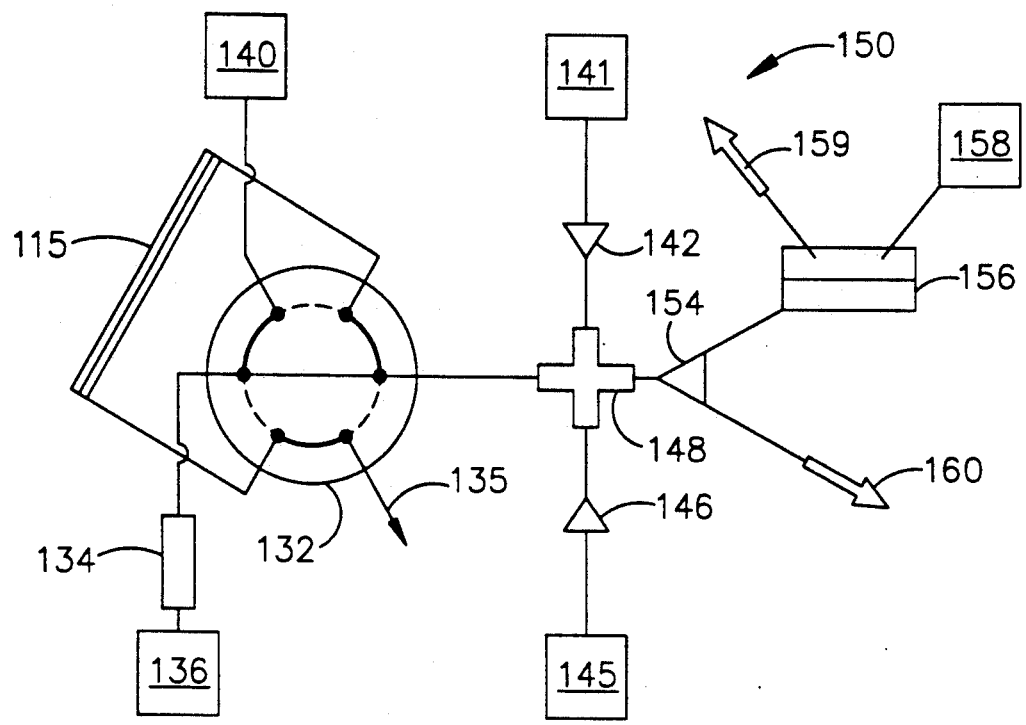
FIG. 4 is a schematic view of an alternative conceptual arrangement incorporating the reversed permeation membrane cell of the present invention, illustrating an automatic analytical system wherein the RPM cell is connected in line with a liquid chromatograph.

FIG. 4 illustrates a conceptual automated analytical system 150 using the reversed permeation membrane technology of the present invention. Particularly, system 150 might preferably comprise a one-sided membrane cell 115 similar to cell 15 described above, and an LC flow cell or column 134 and detector 136 similar to that contemplated in FIG. 2. The RPM cell 115 serves as the sample loop for the LC system (i.e., LC column 134 and detector 136) after collection of the sample, and LC injection valve 132 coordinates the collection and injection procedures. Particularly, it is contemplated that the collected analyte from the reversed permeation membrane cell 115 will be extracted by the mobile phase of the LC system (e.g., 70% acetonitrile, 0.02M $H_3PO_4$). Valve 132 serves as the base around which the system around which the system 150 is set up, and can comprise any of a variety of LC valves, such as available from Rheodyne and Valco. As can be appreciated, sample solution is pumped via sample pump 158 through a cross-flow filter device 156 to valve 132 through cross connector 148 and a three-way flow valve 154. Similarly, flush solvent is provided to valve 132 via pump 145, on/off flow valve 146, and cross connector 148. Extractant solvent is similarly provided through pump 141, on/off flow valve 142, and connector 148.

In operation, the automated analytical system 150 would provide sample solution to valve 132 via pump 158 (e.g., an FMI RSHY pump set at a predetermined flow rate). The sample is directed to reversed permeation membrane cell 115 via valve 132, and from there to waste port 135. Thereafter, flushing is completed by flushing solvent such as water, or a particular solvent mixture (e.g., NNaOH, or inert gas) via flush pump 145 and flow valve 146. Again, this flow is directed through valve 132 to RPM cell 115 and then to waste port 135 (which may or may not be directed to the same waste container to which the sample solution was directed).

Following flushing, extraction is completed by pumping a predetermined volume of extractant solvent into membrane cell 115 via pump 141 and flow valve 142. The extractant solvent is generally allowed to stand within the membrane cell 115 for a predetermined extraction time before it is injected into the LC column 134, such as via eluent pump 140.

Figure 5:
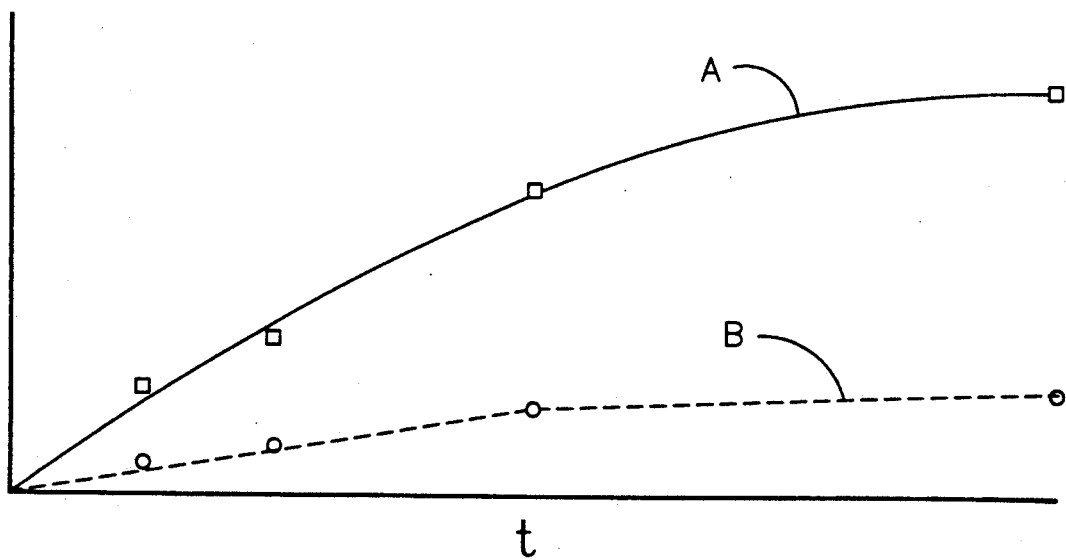
FIG. 5 is a graphical representation of test results from an analytical arrangement similar to that illustrated in FIG. 4, wherein peak analyte detection or concentration of 2,6-dichlorophenol (A) and 3,5-dichlorophenol (B) are plotted against time t (in minutes) of flowing sample.

FIG. 5 illustrates results of flowing sample test results taken on a system similar to that described with respect to FIG. 4. Particularly, this illustration plots the peak heights of detected compounds of interest versus the time of the flowing sample (in minutes) at a flow rate of 0.2 mL/min. The sample solution utilized was acidified water containing 10 ppm of 2, 6-dichlorophenol (line A) and 10 ppm 3, 5-dichlorophenol (line B). The sample pump 158 was allowed to run for varying times of 2, 4, 8 and 16 minutes at the rate of about 0.5 mL per minute, and an extractant solvent comprising 10% acetonitrile and 90% 0.1 NaOH was allowed to stand for 5 minutes before injection. The RPM column utilized comprised a cylindrical membrane support (e.g., 17) having a length of approximately 12 inches (about 304.8 mm) of teflon material, having an inside diameter of approximately 0.03 inches (about 0.79 mm) and an outside diameter of approximately 0.06 inches (1.59 mm). Membrane 20 comprised Silastic silicone rubber tubing fitted within the membrane support and having an inside diameter of approximately 0.02 inches (about 0.5 mm) and an outside diameter of approximately 0.03 inches (0.82 mm).

As can be seen from a review of FIG. 5, it appears that the system begins to reach its equilibrium after about eight minutes, as the concentration curves begin to flatten out. These results also show that the concentration after about eight minutes in a flowing sample is nearly three times the concentration detected after two minutes of flow. Moreover, the concentration factor after eight minutes of flow is nearly ten times the concentration factor of a non-flowing sample at two minutes, as discussed with respect to FIG. 3 above. In this regard, it can be seen that enhanced concentrating capabilities can be obtained utilizing the present reversed permeation membrane invention, wherein a relatively short RPM cell is utilized with a flowing sample to collect and concentrate compounds of interest in a relatively short time period. In this way, not only can very small samples of solution be effectively extracted but much lower concentrations of compounds of interest can also be detected in a quick, automated, and efficient manner by utilizing a flowing sample.

Figure 6:
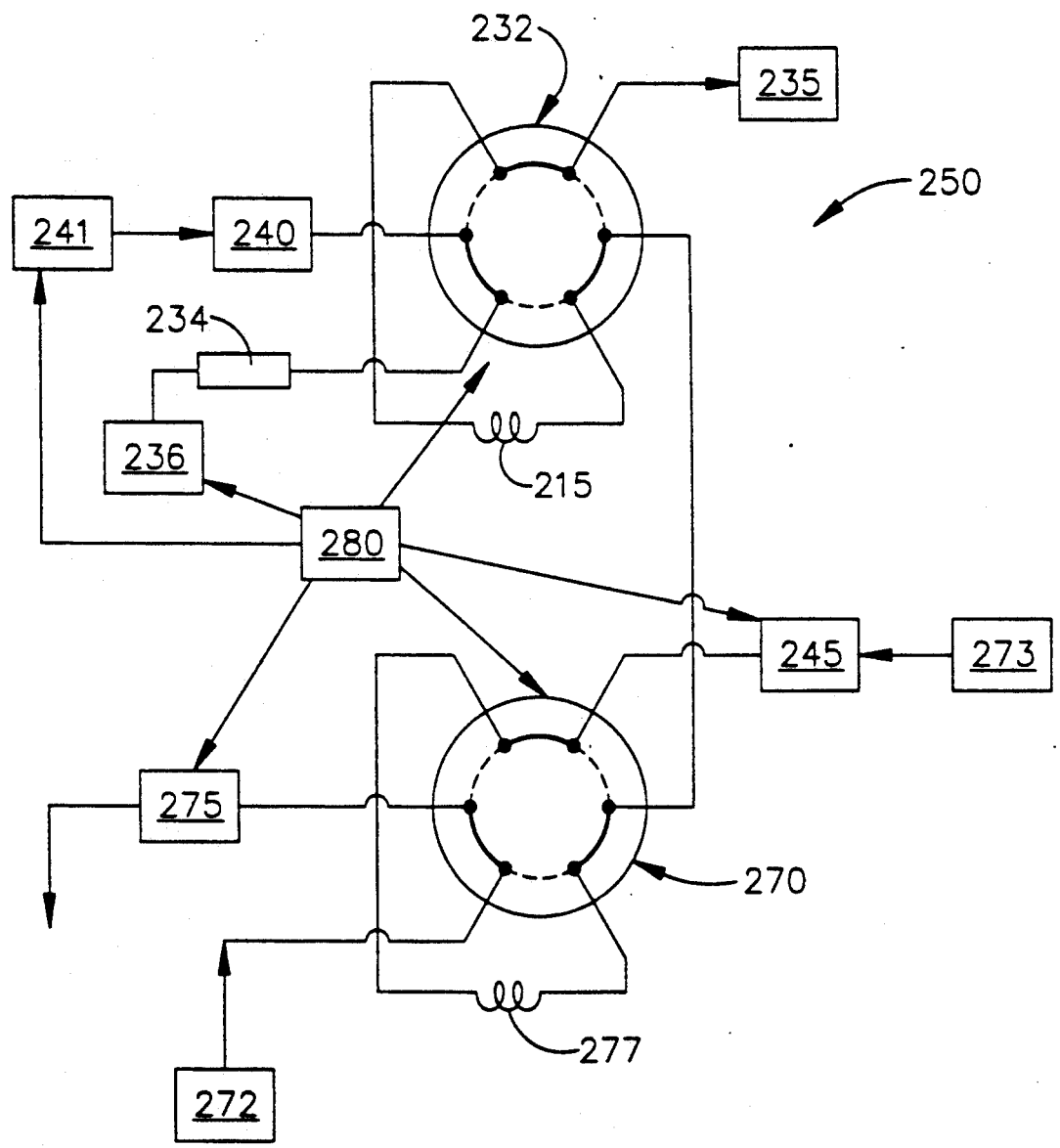
FIG. 6 is a schematic view of another reversed permeation membrane extraction arrangement of the present invention, illustrated in conjunction with a liquid chromatographic (LC) analytical arrangement.

FIG. 6 is a schematic illustration of another preferred embodiment of an on-line application of the subject RPM detection cell. Particularly, FIG. 6 illustrates an automated analytical system 250 wherein RPM cell 215 is connected directly with an LC analytical system. Compounds of interest, such as listed in Tables I and II below, which have permeated into the membrane of cell 215 will be extracted by the mobile phase of the LC system (e.g., an extraction solvent comprising 70% acetonitrile, 0.02M $H_3PO_4$). LC valve 232 is the base of the system, and can comprise a multi-port injection valve such as available from Valco or Rheodyne. A second multi-port valve 270 is utilized to control the flow of sample solution from a sample source 272, as well as the input of water or other flush solvent or gas from source 273. The flush water or solvent can be provided via a pump (e.g., 245), which might preferably be a Kratos Spectroflow 400 Solvent Delivery System, or a Millipore Waters M-45 LC Pump fitted with an Upchurch 40 psi back pressure regulator. Another pump 275 can be provided for facilitating the discharge of waste fluids.

For automatic sample loading, a predetermined volume of sample solution is pulled into a sample loop (e.g., 277) of predetermined volume (e.g., 2.0 mL) by pump 275. For manual sample loading, the injection valve 270 can be fitted with a syringe adapter or the like. LC valve 232 controls the injection of the compounds collected in the RPM cell 215 into an LC system (e.g., LC column 234 and detector 236). The attachment of RPM cell 215 to injection valve 232 can be accomplished by a variety of arrangements known in the industry, however, the attachment must be sufficient to withstand the high pressures of an LC system. For example, where valve 232 comprises a Valco injection valve, it was found that Vespel GC capillary ferrules (as available from Anspec Company), and a standard Valco 0.06 inch (about 1.59 mm) nut perform nicely for this function. Where valve 232 comprises a Rheodyne valve, a teflon tubing spacer was used between the Rheodyne ferrule and the membrane support of the RPM cell 215. It is contemplated that a variety of other arrangements will also be effective to connect the RPM cell of the present invention in-line with LC, GC and other high pressure/temperature analytical devices. FIG. 6 shows valves 232 and 270 configured so that valve 270 is in its sample collection mode (sample from source 272 being loaded into loop 277), while valve 232 is in its inject mode (extractant from source 241 being provided through cell 215 directly to column 234 for analysis). Alternate valve pathways (e.g., for sample flow to cell 215 and flushing) are indicated by dashed lines.

In tests completed utilizing an automatic loading configuration similar to that shown in FIG. 6, the LC system comprised a Millipore Waters M-45 LC pump and a Kratos spectroflow 773 detector, wherein the wavelength of detection could be either 210 or 254 nm. A Microsorb Dynamax 3 micron, C-18, 4.6×100 mm column (as available from Rainin Instrument Company) was used to determine the presence of chlorobenzenes, while a Brownlee RP-8 10 micron, C-8 4.6×10 cm column in a Brownlee spheri-5 5 micron, 4.6×3 cm guard cartridge (as available from Anspec Company) was used to determine the presence of PAH compounds. For both columns the mobile phase was 70% acetonitrile, 0.02M $HP_3O_4$, and data collection and analysis was completed on a Spectra-Physics SP 4270 integrator. For the set-up utilizing Valco type injection valves, valve switching was completed automatically via a Valco digital valve interface and the external control option on the Spectra-Physics SP 4270 integrator (these devices schematically illustrated in FIG. 6 as control 280).

In use, the RPM sampling was initiated by injection of the sample solution via valve 270. After the sample solution had flowed within RPM cell 215 for a predetermined sampling time, a water flush was completed by loading water from source 273 via pump 245 and valve 270. Thereafter, valve 232 permitted injection of the mobile phase eluent from source 241 via LC pump 240. Due to the relatively thinner membrane thickness and small internal diameter of the capillary sized tubes utilized, it was found that following sample dwell time and flush procedures, the flow of extractant could be pumped without interruption (i.e., without holding extractant within cell 215) through cell 215 and into the LC column. The ability to extract on a continuous, or non-stop basis is believed to be a significant breakthrough in extraction/analysis procedures of this type. The mobile phase completed extraction of permeated compounds from the membrane of cell 215 and was thereafter provided directly to LC column 234 for chromatographic separation. The data obtained from LC separation testing provided chromatograms exhibiting sharp peaks due to the focusing of compounds of interest on the LC column. It was found that the focusing characteristics was a result of collection and concentration of the compounds in RPM cell 215, and that after extraction, collected compounds elute as a very compact sample plug into the LC column.

As mentioned above, the material from which semipermeable membrane 20 is constructed will provide a certain degree of selectivity of compounds thereby providing a first level of selecting compounds of interest to be analyzed. When the sample solution is placed into contact with the supported membrane 20, the compounds of interest dissolved in the sample solution permeate into the membrane, while the balance of the residual sample matrix is expelled from the membrane cell 15 as it is flushed out by continuing flow of the sample, and, eventually, by a flush solvent. The selectivity of the membrane is a result of differing water partition coefficients between the various elements of the solution and the membrane interface. In order that a compound will preferably permeate into the membrane, the coefficient must favor the membrane, as opposed to the solution. The partition coefficient between the solution and membrane interface can be determined by the following equation:

$$P_s = ([X]_M/V_M)/([X]_s/V_s)$$

Where
- $[X]_M$ and $[X]_s$ are respective concentrations of a compound X in the membrane and in the sample solution.
- $V_M$ and $V_s$ are the volumes of the membrane and sample solution phases, respectively.

For example, the efficiency of collection and recovery of chlorobenzenes and PAH compounds (which are two groups of compounds of particular general environmental interest) are listed below on Tables I and II for several different membrane configurations. Particularly, the OV-1 film is 100% dimethylpolysiloxane, while the DB-5 material is more polar and comprises 5% diphyenyl and 95% dimethyl-polysiloxane. The SE-30 is a silicone-based oil which is not cross-linked, and the DB-624 comprises cyanoproyl, phenol, dimethyl-polysiloxane polymer film.

TABLE I

Efficiency Data for Chlorobenzenes on various RPM Columns

| Rpm Column Type membrane/length/thickness/i.d.source | | A | B | C | D | E | F |
|---|---|---|---|---|---|---|---|
| 1 min water flush | | | | | | | |
| 20 cm OV-1 | 5 um 0.32 mm i.d. Quadrex | 8 | 20 | 36 | 51 | 56 | 55 |
| 40 cm OV-1 | 5 um 0.32 mm i.d. Quadrex | 12 | 34 | 56 | 70 | 72 | 66 |
| 90 cm OV-1 | 5 um 0.32 mm i.d. Quadrex | 24 | 62 | 82 | 93 | 96 | 88 |
| 510 cm OV-1 | 7 um 0.53 mm i.d. Restek | 63 | 67 | 72 | 76 | 76 | 71 |
| 233 cm SE-30 | 14.5 um 0.53 mm i.d. Not cross-linked | 54 | 61 | 65 | 68 | 68 | 64 |
| 2 min water flush | | | | | | | |
| 90 cm OV-1 | 5 um 0.32 mm i.d. Quadrex | 9 | 53 | 81 | 91 | 90 | 83 |
| 90 cm OV-1 | 7 um 0.53 mm i.d. Restek | 59 | 76 | 79 | 83 | 80 | 77 |
| 90 cm DB-5 | 5 um 0.32 mm i.d. Heliflex | 14 | 65 | 86 | 93 | 91 | 86 |
| 90 cm DB-5 | 5 um 0.32 mm i.d. Heliflex | 12 | 61 | 81 | 90 | 87 | 80 |
| 90 cm DB-5 | 1 um 0.32 mm i.d. Restek | 0 | 9 | 45 | 80 | 86 | 79 |
| 90 cm DB-624 | 1.8 um 0.32 mm i.d. J & W | 1 | 28 | 69 | 87 | 87 | 78 |
| 7 min water flush | | | | | | | |
| 90 cm OV-1 | 7 um 0.53 mm i.d. Restek | 17 | 58 | 71 | 77 | 77 | 73 |
| 233 cm OV-1 | 7 um 0.53 mm i.d. Restek | 53 | 71 | 76 | 80 | 80 | 75 |

A = benzene
B = chlorobenzene
C = 1,2-dichlorobenzene
D = 1,2,3-trichlorobenzene
E = 1,2,3,4-tetrachlorobenzene
F = pentachlorobenzene The tests of Table I were obtained on an experimental device shown and described with respect to FIG. 6 above, wherein a six minute sampling time was utilized with a 0.58–0.99 ppm concentration level of chlorobenzenes, and a flow rate of 0.20 mL per minute. Similarly, Table II shows test results from an experimental set-up utilizing a six minute sampling time with a solution of 160–240 ppb concentration of PAH compounds in 10% methanol, with an RPM flow rate of 0.2 mL per minute. The individual stock solutions of the chlorobenzenes and PAH compounds were prepared by dilution of the compound in acetonitrile (e.g., Fisher HPLC grade). Particular solutions of the chlorobenzenes were then prepared by dilution in water of the indicated parts per billion stock solutions of each compound, while the PAH compounds were prepared by dilution of the indicated parts per million stock solutions in 10% methanol (e.g., Baxter High Purity) due to the low solubility of PAH compounds in water.

TABLE II

Efficiency Data for PAHs on various RPM Columns

| RPM column membrane/length/thickness/source | | G | H | I | J | K |
|---|---|---|---|---|---|---|
| 2 min water flush | | | | | | |
| 20 cm OV-1 | 5 um 0.32 mm i.d. Quadrex | 30 | 43 | 42 | 21 | 23 |
| 40 cm OV-1 | 5 um 0.32 mm i.d. Quadrex | 50 | 61 | 58 | 14 | 5 |
| 90 cm OV-1 | 5 um 0.32 mm i.d. Quadrex | 70 | 79 | 72 | 20 | 7 |
| 90 cm DB-5 | 1 um 0.32 mm i.d. Restek | 43 | 71 | 71 | 26 | 14 |
| 90 cm DB-5 | 5 um 0.32 mm i.d. Heliflex | 77 | 84 | 77 | 20 | 7 |
| 90 cm DB-624 | 1 um 0.32 mm i.d. J & W | 60 | 77 | 73 | 25 | 14 |
| 90 cm phenyl-methyl | deact 0.32 mm i.d. Restek | 2 | 4 | 9 | 10 | 6 |
| 90 cm OV-1 | 7 um 0.53 mm i.d. Restek | 78 | 81 | 73 | 21 | 9 |
| 7 min water flush | | | | | | |
| 88 cm OV-1 | 7 um 0.53 mm i.d. Restek | 63 | 75 | 71 | 23 | 20 |
| 233 cm OV-1 | 7 um 0.53 mm i.d. Restek | 73 | 82 | 75 | 33 | 21 |
| 510 cm OV-1 | 7 um 0.53 mm i.d. Restek | 78 | 86 | 82 | 53 | 44 |
| 233 cm SE-30 | 14.5 um 0.53 mm i.d. not crosslinked | 79 | 89 | 85 | 41 | 31 |

G = Acenaphthylene
H = Phenanthrene
I = Fluoranthene
J = Benz[a]anthracene
K = Benzo[b]fluoroanthene As will be understood, as the sample solution passes through RPM column 215, the compounds of interest permeate into the membrane film, the diffusion coefficient and the partition coefficient of the membrane/solution interface governs the amount of each compound which is permeated into the membrane at any point along the sample plug. It has been found that initially, efficiency of the permeation of the compound into the membrane film is relatively high due to the correspondingly high partition coefficient for the interface. However, eventually the system approaches a steady state and the efficiency of permeation begins to decrease or level off. This leveling off is also governed by the partition coefficient between the interface. While it has been found that slower flow rates appear to enable more efficient permeation into the membrane as a result of longer contact time per unit area of the membrane, it has also been observed that the ability to collect sample compounds utilizing a fast flowing sample permits the collection and analysis of much lower concentration levels (e.g., parts per billion (ppb) and parts per trillion (pptr)) in shorter periods of time.

There are two approaches to considering and utilizing sample flow rates. As has been discussed, the highest efficiency of extraction occurs at low flow rates of sample through the RPM column (e.g., 0.1 mL/min). However, at lower flow rates, a corresponding relatively smaller sample volume will pass through the RPM (e.g., 0.1 mL/min × 10 min = 1 mL). As a result, the absolute amount of analyte available for extraction is reduced for a specific sampling time. It has been shown that if faster flow rates (and correspondingly larger sample volumes) are used, the absolute amount of the analyte collected is greater in the same time period even though the collection efficiency is reduced. This effect was illustrated by testing the following mixture of compounds in the 10 to 20 ppb concentration range.

| | | |
|---|---|---|
| 1. | Acenaphthalene | 10 ppb |
| 2. | Phenenthrene | 10.7 ppb |
| 3. | Fluoranthene | 10 ppb |
| 4. | 1,3,5-Trichlorobenzene | 23 ppb |
| 5. | 1,2,3,4-Tetrachlorobenzene | 18.5 ppb |
| 6. | Pentachlorobenzene | 12.5 ppb |
| 7. | Hexachlorobenzene | 12.5 ppb |

A water solution containing the above compounds were pumped through a 75 cm RPM column, with a 7 um thick membrane for 5 minutes at different flow rates. The collected analytes were then analyzed. The amounts collected at a 4 mL/min flow rate were about four (4) times the amount collected at a 0.34 mL/min flow rate, and an estimated sixteen (16) times the amount collected at a 0.1 mL/min flow rate. This would allow better detection limits or shorter sampling times and/or RPM column lengths for the same detection limits.

Consequently, while the efficiency of permeation and collection increases as the flow rate decreases (i.e., as the contact time is increased), efficiency of collection is not always critical, as more consistent sample solutions and higher sensitivity to low concentrations can be accomplished in a shorter amount of testing time utilizing a flowing sample in the present invention. In effect, it has been found that an extraction test which would normally require as much as one liter or more of sample solution, 40–50 mL or more of solvent, and 1–2 days of relatively manpower intensive testing procedures, can be automatically completed and reported within an hour or less with an automated configuration such as shown and described with respect to FIGS. 6 and/or 7 above. As illustrated in the test results described above, RPM cells made in accordance herewith and having a length of one meter or less have been shown to obtain extraction results comparable or better than those previously provided by devices and procedures which required collection columns of 15 to 50 meters length.

As can be appreciated, the reduced column length required for the RPM extraction procedures of the present invention simplify preparation, use and handling of the physical equipment and procedures involved, reduce the costs of the columns themselves, and enable relatively easy storage and transportation of RPM cells to remote sensing locations for collection of samples. Particularly, it is contemplated that RPM cells made in accordance herewith, and generally having an operational length of approximately 1 meter or less, can easily be transported to a remote collection site where a predetermined volume of sample solution can be run through the columns on site. Thereafter, the columns are returned to the laboratory for extraction and separation procedures. In this way, a relatively large volume of sample solution could be tested for very low concentrations of trace elements without a need to transport large quantities of sample solution between the site and the laboratory.

Figure 7:
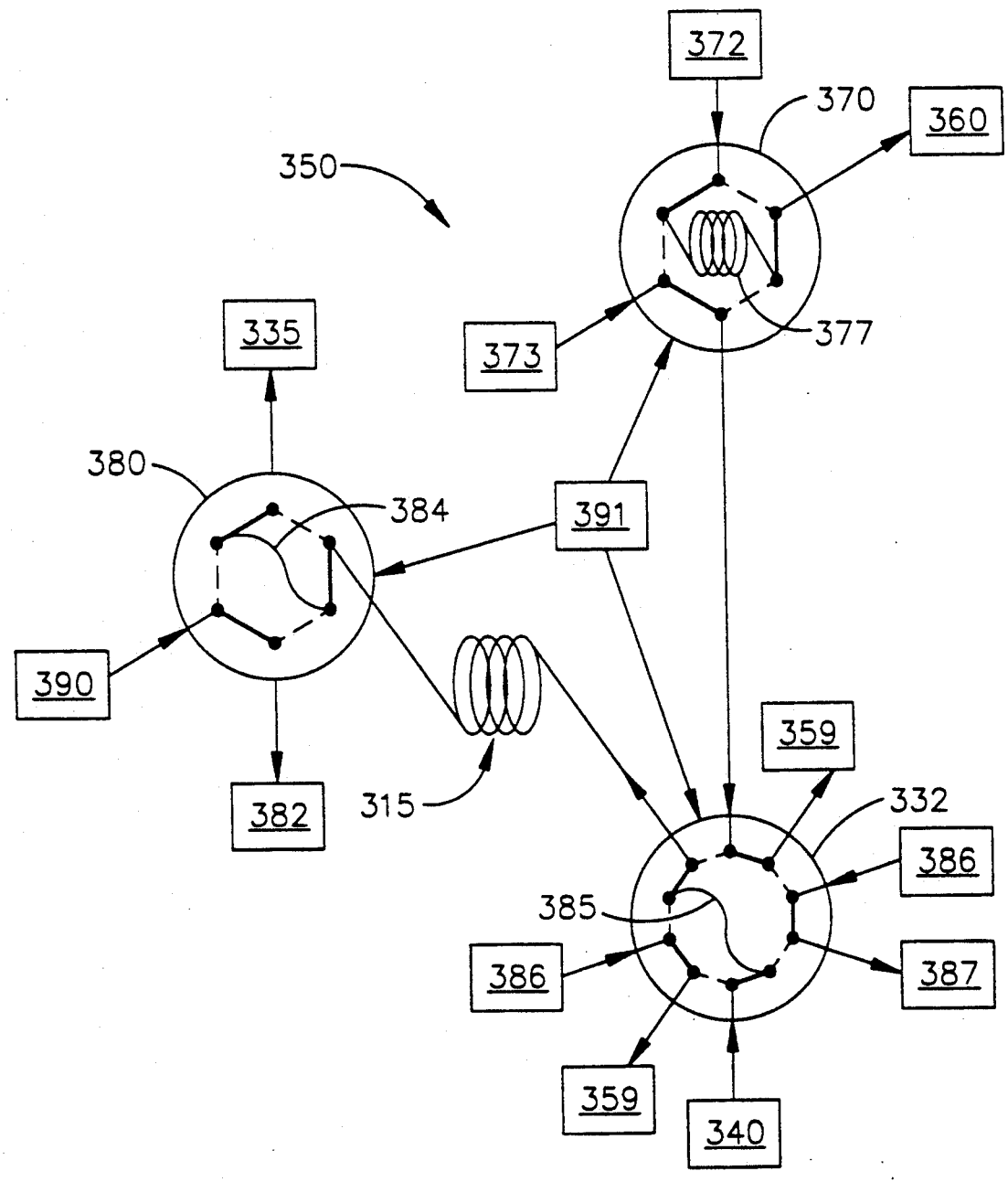
FIG. 7 is a schematic view of an automatic reversed permeation membrane extraction arrangement made in accordance herewith, illustrated in conjunction with a gas chromatography/mass spectrometry analytical arrangement.

It is also contemplated that the present RPM collection and extraction process can be similarly utilized in-line with gas chromatography/mass spectrometry (GC/MS) analyzing devices for trace organics. Particularly, FIG. 7 illustrates a schematic illustration of an RPM/GC/MS air-segmented interface utilizing three pneumatically actuated multi-port valves. This arrangement illustrates a preferred arrangement for integrating the present invention with the GC/MS hardware, while incorporating an air segment to separate the sample solution from the organic extractant solvent.

Referring to the analysis system 350 of FIG. 7, sample solution is loaded into sample loop 377 of valve 370 from a source (e.g., 372), and a pump (e.g., 373) pushes the sample to valve 332 where it is directed through RPM cell 315. After the predetermined sample volume from loop 377 has contacted RPM cell 315, and cell 315 has been appropriately flushed, valve 332 is switched to allow extractant solvent to pass through cell 315 such as via eluent pump 340. Preceding the injection of the extractant solvent, however, it is contemplated that valve 332 will pass an air segment through RPM cell 315 to limit the diffusion of organic elution front into the wash or sample solution, to minimize the probability of water being injected into the GC device, and to facilitate flow rate measurement for timing of the valve switching events themselves. Air gap loop 385 is provided to dose the volume of air to be passed through the RPM cell. The extractant solvent is pumped into the GC sample loop (e.g., 384) and injected into GC/MS analyzing device 382 via valve 380.

A number of tests were run on a device similar to that shown and described with respect to FIG. 7, wherein the first 100 uL of eluent exiting RPM cell 315 was injected into the GC device 382. In the testing arrangement, valves 370 and 332 were controlled by a Spectro-Physics SP 4270 integrator, while valve 380 was controlled by the GC/MS hardware. FIG. 7 collectively illustrates the controlling hardware schematically as controller 391. RPM cell 315 was provided as a 100 cm long cylindrical tube of approximately 0.53 mm inside diameter, and having a 7 um film membrane of Restek RTX-1 poly(dimethylsilicone). The sampling time was 12 minutes at approximately 0.3 mL per minute flow rate, while the air gap volume was 10 uL. The extractant solvent utilized was 100% acetonitrile. The GC/MS hardware comprised an HP 8590-II GC/5971A MS, with a GC injection loop volume of 100 uL, an LOCI retention gap of 15 meters by 0.53 mm inside diameter (intermediate polarity deactivated), and the analytical GC column was 30 meters long with a 0.25 mm inside diameter and a 0.25 um film (Restek RTX-5). Additional parameters utilized for the experiment included an LOCI divert time of 1.40 minutes and a heat time of 2–10 minutes, with GC temperatures of 85° C. isothermal for 7 minutes, then 20° C. per minute increase to 85° C. The MS conditions included scan range of 45–300 m/z at two scans/second (Emv=1729 volts).

Figure 8:
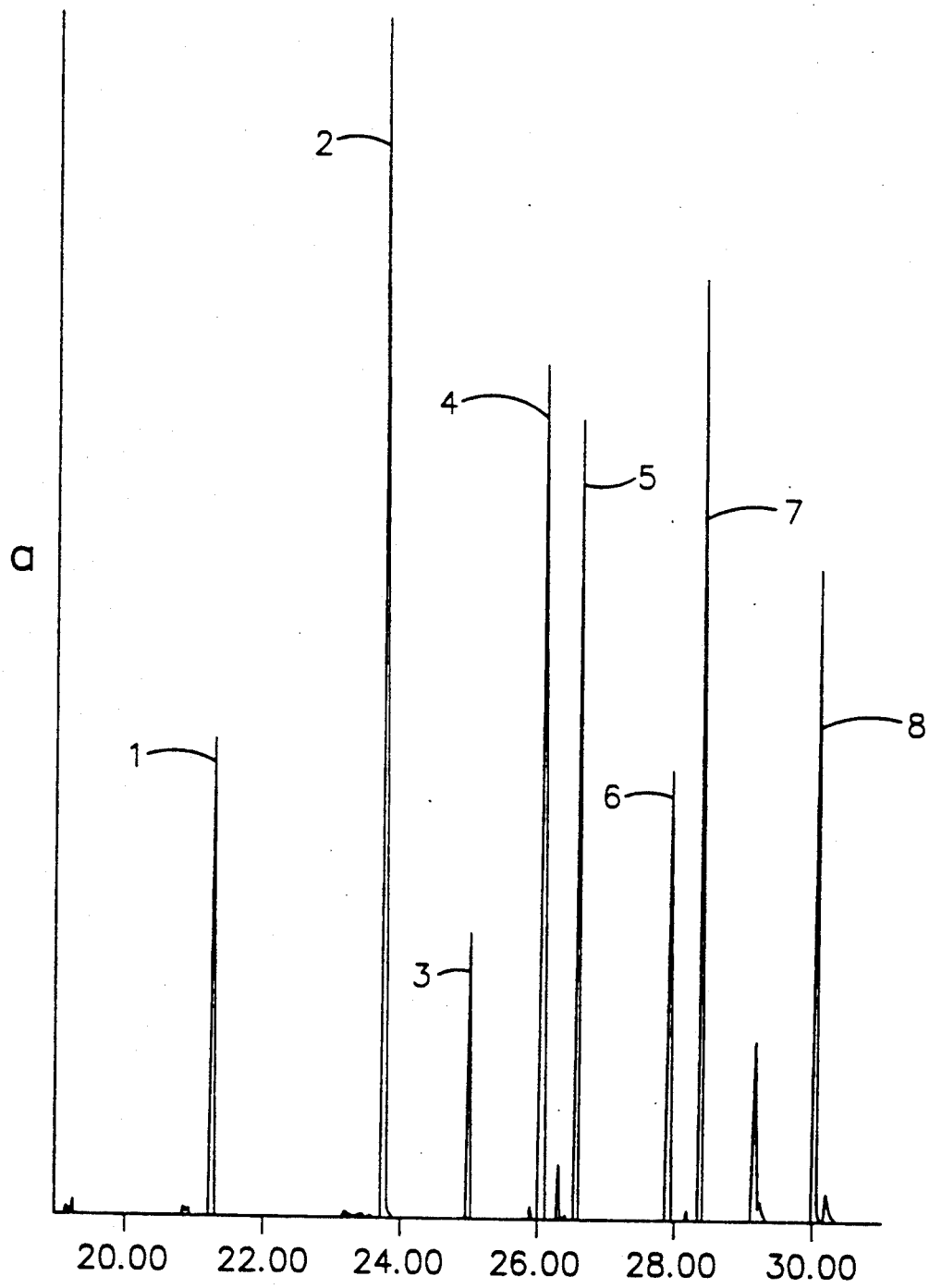
FIG. 8 is a reconstruction total ion current (TIC) chromatogram for an RPM/GC/MS analysis of trace organics in a water sample wherein abundance (a) is plotted against M/Z.

The reconstructed total ion current (TIC) chromatogram for the RPM/GC/MS analysis performed on the device described above is shown in FIG. 8, where abundance (a) is plotted against scan M/Z. The eight peaks shown in FIG. 8 represent the direct analysis of the following analytes and their concentrations:

| Peak | Analyte | Concentration (ppb) |
|---|---|---|
| 1. | 1,2-Dichlorobenzene | 15.0 |
| 2. | 1,2,3-Trichlorobenzene | 19.2 |
| 3. | 1,2,4,5-Tetrachlorobenzene | 13.8 |
| 4. | Acenaphthalene | 11.4 |
| 5. | Pentachlorobenzene | 11.7 |
| 6. | Hexachlorobenzene | 10.8 |
| 7. | Phenanthrene | 12.4 |
| 8. | Fluoranthene | 12.0 |

This example documents the fact that the apparatus and process of the present invention can selectively extract analytes of interest from aqueous and non-aqueous samples for direct transfer to a gas chromatograph/mass spectrometer for on-line separation, identification and quantification. The RPM extraction process provides for the transfer of collected analytes with organic solvents which are compatible with GC analysis. The sampling, transfer and GC/MS analysis is completely automated for on-line and unattended operation if desired. In this way, the attributes of the present RPM extraction technology and its selective analyte collection can be directly combined with the separation power, sensitivity and selectivity afforded by large volume on-column injection high resolution GC/MS technology. The amount of analyte collected by the RPM cell may be selected and controlled by adjustment of the sample volume, the flow rate, the extractant solvent, etc., and an extremely wide range of analyte concentrations may be assayed with this device. Very low limits of detection (i.e., in the low parts per trillion (pptr) range or lower) are attainable utilizing the present RPM invention.

It has further been found that as a result of the relatively short column lengths, and the ability to quickly flush residual sample solution and rapidly recover analytes permeated into the RPM cell membrane, the present RPM capillary cells feature rapid recovery and essentially no carryover between successive testing operations. Consequently, successive tests can be manually or automatically performed without requiring inconvenient and laborious disassembly and cleaning operations. As mentioned above, due to the strengthening nature of the non-porous membrane support of the present invention, membranes of widely varying chemical and physical make-up can be utilized to augment the selectivity and control of the concentration and extraction process. By simplifying and speeding up the trace component analysis testing procedures, and by providing virtually unlimited opportunities for improving selectivity of compounds collected and detectible concentrations, analysis of various fluids such as wastewater and the like is improved, as is the ability to monitor the quality of industrial effluents, drinking water, ground water runoff, etc.

Additional testing has been undertaken to study the various parameters of the subject RPM extraction device and process. As mentioned, the collection characteristics of an RPM cell are dependent on parameters such as column length, thickness of the semi-permeable membrane, composition of the membrane, and diffusion rates (i.e., the solubility plus diffusion rate) of the individual compounds to be collected. The amount of each compound collected also depends on its concentration, the flow rate of the sample, the sampling time and the temperature.

For example, the collection time is one of the critical parameters that effect the compounds of interest collected within the RPM cell. During the collection of PAH compounds on a 90 cm OV-1 RPM cell (for concentrations of approximately 180–240 ppb of the PAH compounds) for example, it was found that the peak collection begins to level off at about 12 minutes of sampling time for acenaphthylene, phenanthrene, and fluoranthene. The loading of the other PAH compounds is much lower and does not level off. On the other hand, in a sampling time-dependence test concerning the collection of chlorobenzenes (0.6–1 ppm concentration) within RPM cell 233 cm in length (7 um OV-1) and 0.53 mm in inside diameter, it was found that only the collection of benzene appeared to level off at about 12 minutes of sampling time, while the RPM cell continued to concentrate the other chlorobenzenes. It is believed that the leveling effect observed for the permeation of benzene may have resulted from a rapid equilibrium in the film.

As the molecular weight of permeating compounds increases, the diffusion rate through the film correspondingly decreases, thereby causing equilibrium within the membrane to be reached more slowly. With regard to the collection of benzene, the limiting factor appears to be its rapid equilibrium within the membrane. In contrast, the PAH compounds having greater molecular weights are limited by their diffusion rate within the membrane. During a particular sampling period, lower diffusion rates lead to a lower permeation of the compounds and slower equilibrium. In this respect, it has been found that an increase in film thickness tends to improve the efficiency for collection of chlorobenzene and 1,2-dichlorobenzene, but has little effect on 1,2,4,5-tetrachlorobenzene and pentachlorobenzene. Moreover, sampling time of collection through an RPM cell can also be adjusted to access a wide range of sample concentrations. For example, a highly concentrated sample can be assayed utilizing a relatively short sampling time, while a longer sampling time, or flowing sample (i.e., larger volume of sample), can better determine trace analysis on the same RPM cell.

As discussed above, once the compounds of interest are collected from the sample solution, the residual sample matrix is preferably flushed from the column with the use of a flush solvent or gas. While use of a flush solvent provides a faster and more thorough cleaning of the RPM cell, it may also cause reverse permeation of collected analytes back into the flush solvent. In order to minimize undesired loss of analyte, the partition coefficient for the membrane/solvent interface must favor the membrane. The amount of solvent should also be minimized, and the total volume will depend upon the internal volume of the RPM cell itself. As mentioned above, some selectivity as to permeated compound loss can be obtained by proper choice of flush solvent. For example, the concentration of permeated compounds which are more soluble in water (e.g., benzene, chlorobenzene, acenaphthylene, etc.) can be reduced or eliminated by utilizing a water based flush solvent, and by increasing the water flush time.

In most situations, the flush step of the present process is necessary to remove the particulates and other interferences found in the sample matrix. If these are not present, or are removed by some pre-treatment, the flush step may be eliminated. Additionally, it may be desirable not to use the flush step in setups where the RPM cell acts like an LC loop injector for compounds which are not extracted by the RPM while concentrating compounds which are extracted. In this dual mode, both types of compounds may be analyzed in one injection.

Tests varying the length of the RPM cell column length show that there does not appear to be any significant effect on the rate of loss of permeated compounds due to varying column length. On the other hand, longer column lengths typically result in additional capacity and better efficiency for collection of particular analytes due to the increase in membrane volume and contact area. With respect to the collection of chlorobenzenes, it has been seen that as column length increases from about 20 cm to about 90 cm, the amount of collected compound increases for all of the priority chlorobenzene pollutants discussed above. Further increases in column length from about 90 cm to about 510 cm, however, have less effect for most of the chlorobenzenes, as a leveling-off effect becomes evident between about 230 cm and 510 cm. Because it would be expected that increasing column length should continue to increase the efficiency of collection up to 100%, this leveling off is indeed unexpected and is believed to be likely due to the slow diffusion of the compounds of interest within the sample solution plug as it passes through the RPM cell. Particularly, as the sample plug passes through the cell, an essentially laminar concentration profile develops, and only the compounds on the outer portion of the profile will permeate into the membrane. The compound molecules in the inner portion of the plug must diffuse outwardly to contact the membrane. The limitation of slow diffusion would be exacerbated as the column diameter increases, and can be minimized by decreasing the column diameter and/or by increasing the temperature or turbulence of flow therewithin (e.g., adding glass beads or other inert material within the column).

A similar leveling-off effect was discovered with the PAH compounds acenaphthylene, phenanthrene, fluoranthene, and benz[a]anthracene with 233 cm long columns. Although some increase in efficiency is observed for a few compounds by utilizing longer RPM columns (e.g., 200-500 cm), it has been observed that the amount of increase is not directly proportional to the increase in length. While RPM column lengths of up to 5 meters or so may have slight advantages for a few compounds, lengths of less than about 2 meters, and most preferably about 1 meter or less, are optimum for most applications.

The thickness of the membrane of the present RPM cell can also be adjusted for selectivity and efficiency purposes. For example, for the chlorobenzene compounds being collected on the DB-5 material discussed above, a thicker membrane was found to increase amounts of collected compounds. It is believed that this increase is due to the increased volume of such thicker membrane, which results in a more favorable partition coefficient between the membrane and the analyte in accordance with the equation set forth above. The magnitude of the increase of collected PAH compounds with thicker membranes decreases for more non-polar compounds. In fact, for the compounds benz[a]anthracene and benzo[b]fluoranthene, there is actually a slight decrease of collected compound with an increase in membrane thickness. In contrast, varying the membrane thickness of the SE-30 material had no effect for collection of PAH compounds. Increased collection of compound with increased thickness of the membrane results only when the compound can diffuse through the membrane at an acceptable rate. Depending upon the diffusion rate of the analyte, further increases in membrane thickness have negligible effects as the compounds never permeate far enough during the sampling time for the additional thickness to make a difference.

As set forth above in Tables I and II, smaller RPM cell diameters show increases in compound collection with increased sampling time. As discussed above, this appears to be the result of smaller diffusion distances within the sample plug, minimizing the leveling-off effects for longer length columns. For larger diameter columns (which may be required with thicker membranes) the addition of glass beads or other inert fillers should overcome any sample plug diffusion limitations which might otherwise result from the larger diameters.

Tests on collection of chlorobenzenes and PAH compounds in experimental RPM cells made in accordance herewith show that good linearity of collection of chlorobenzenes is observed from between at least about 64 ppb and about 2.75 ppm, while good linearity of collection of PAH compounds was seen between at least about 20 ppb and about 420 ppb. Consequently, a variety of RPM cell parameters can be adjusted to provide additional selectivity for optimizing the determination of trace organics in sample solutions such as water. It should also be noted that the diffusion rate of various compounds into the semi-permeable membrane will change with varying temperatures, as will the solubility of the compounds in the membrane, flush solvent, and extract solvent. Control of test temperatures can thereby provide additional selectivity for the present extraction method.

The effect of temperature on RPM extraction operations was investigated using an RPM/LC configuration similar to that shown in FIG. 6. In this experiment, the RPM cell comprised an 88 cm long, 0.53 mm i.d. fused silica capillary with a 7 um thick 100% poly(dimethylsiloxane) (i.e., Rtx-1) membrane. The membrane was thermostated using a proportional band temperature controller, and sample solution was pumped through the RPM column for 6 minutes at a flow rate of 0.2 mL/min. The analytes were then extracted using an acetonitrile/water solution and analyzed on a HPLC column using UV detection.

An aqueous sample solution containing the following organic analytes at the listed concentrations was used as a test mixture.

| | TEST MIXTURE | |
|---|---|---|
| (FIG. SYMBOL) | COMPOUND | CONCENTRATION (ppb) |
| b | benzene | 150 |
| c | monochlorobenzene | 150 |
| di | 1,2-dichlororbenzene | 150 |
| tr | 1,2,3-trichlorobenzene | 192 |
| te | 1,2,4,5-tetrachlorobenzene | 138 |
| p | pentachlorobenzene | 117 |
| h | hexachlorobenzene | 108 |
| a | acenaphthalene | 144 |
| ph | phenanthrene | 124 |
| f | fluoranthene | 120 |

Figure 9:
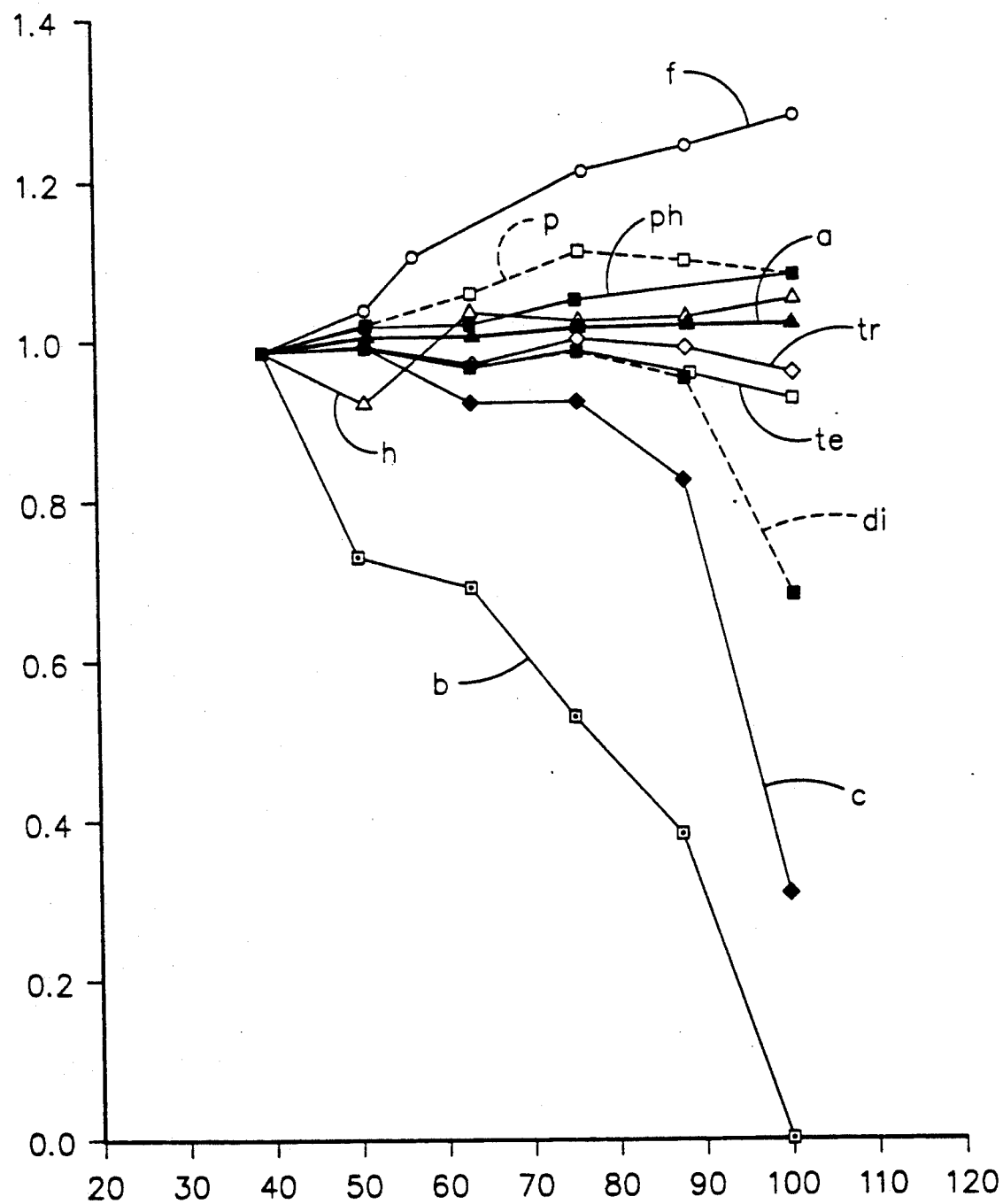
FIG. 9 is a graphical representation of test results illustrating temperature effects on RPM extraction according to the present invention, where analyte signal is plotted against temperature (°C.)

Experiments were performed at approximately 20° C. intervals in the temperature range between about 37.5° and 100° C. The analyte signal (LC peak height normalized to 37.5° C.) is plotted as a function of temperature (°C.) in FIG. 9. To clearly display relative effects of temperature, the analyte peak heights were normalized to the intensity obtained at 37.5° C. The results in FIG. 9 show that the analytical response for benzene, chlorobenzene, and 1,2-dichlorobenzene decreases as the RPM cell temperature increases. The attenuation is most significant for benzene, followed by chlorobenzene and dichlorobenzene. The attenuation appears to scale with relative analyte vapor pressure or boiling point. The higher molecular weight chlorobenzenes exhibited relatively minor changes in signal over the temperature range studied. In contrast, the PAH response was enhanced at higher temperatures. From this study it is clearly seen that RPM temperature may be tailored to increase the selectivity and sensitivity of certain compounds.

A study was also conducted to investigate the effects of organic solvents in the sample solution. The studies were performed at ambient temperature using an RPM/LC configuration similar to that shown in FIG. 6. In this experiment, the RPM cell comprised an 88 cm long, 0.53 mm i.d. fused silica capillary with a 7 um thick 100% poly(dimethylsiloxane) (i.e. Rtx-1) membrane. Sample solution was pumped through the RPM cell for 6 minutes at a flow rate of 0.2 mL/min. After sampling, the RPM cell was flushed with pure water for 2 minutes at 0.2 mL/min. The analytes were then extracted using an acetonitrile/water extraction solution and analyzed on an HPLC column using UV detection.

Solvent solutions studied included acetone/water, acetonitrile/water, methanol/water and 2-propanol/water. Sample solutions were prepared having 0, 5, 10, 20, 40, 60, 80 and 100% (v/v) organic solvent content, respectively. Analyte mixtures were prepared in binary organic-solvent/water solutions with concentrations as listed above for the Test Mixture.

An example of data for an acetonitrile/water solvent system is shown in FIGS. 10A and 10B where the analyte signal (LC peak height normalized to 37.5° C.) is plotted against % (v/v) of acetonitrile. Analyte LC peak heights were normalized to the response obtained from the mixture prepared in pure water (0% organic). As can be seen, for most analytes, the collection efficiency generally increases as the organic content of the matrix is increased from 0% to about 20% acetonitrile, where maximum response was observed. The relative collection efficiency begins to generally and rapidly decline above acetonitrile concentrations of approximately 20%. In general, the analyte response is less than that from pure water when the acetonitrile content exceeds approximately 60%.

The extent of signal enhancement, as well as the organic solvent content at which maximum signal is attained, is analyte dependent. For example, benzene exhibits a maximum response enhancement of about 10% relative to pure water. This occurs when the sample matrix contains 10% acetonitrile. On the other hand, the collection efficiency or response is increased approximately 200% (relative to pure water) for 1,2,4,5-tetrachlorobenzene and pentachlorobenzene when the sample solution contains 20% acetonitrile.

Figure 11B:
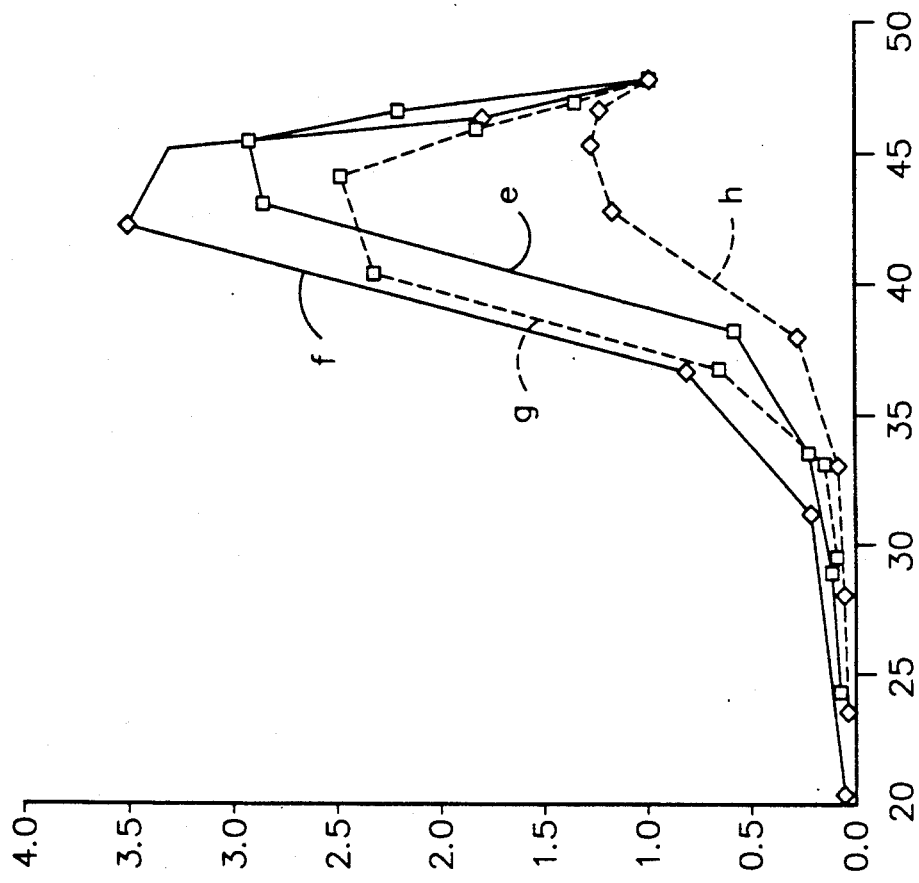
Figure 11A:
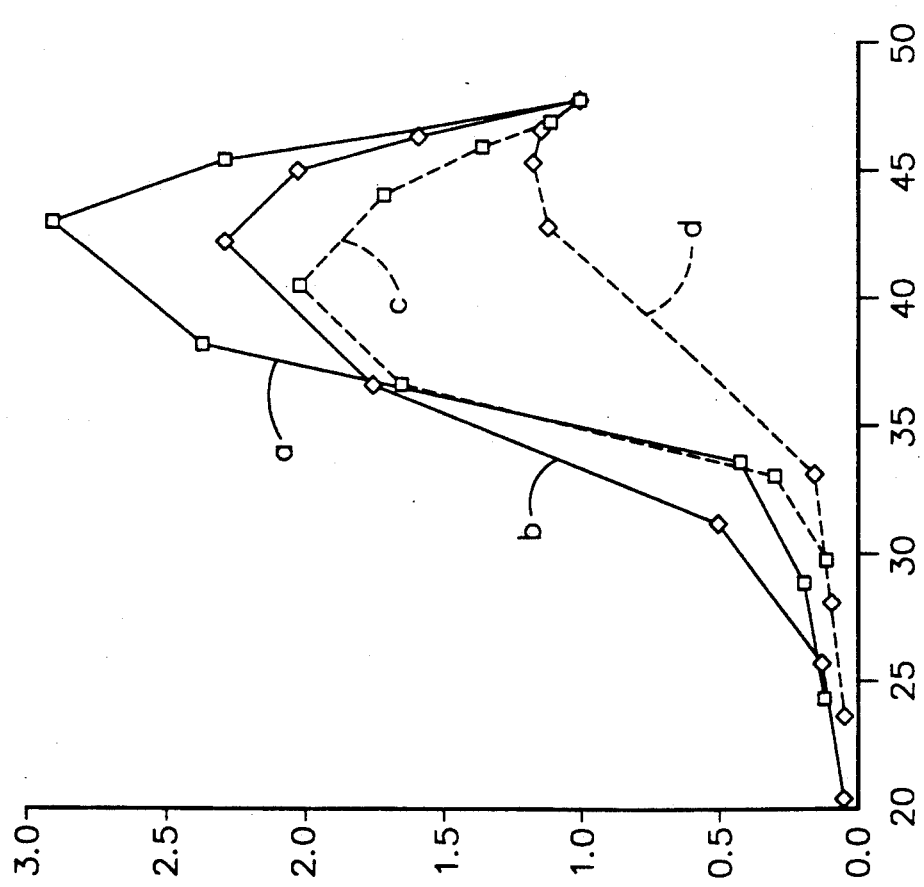

Similar enhancement effects were also observed in the acetone/water, methanol/water and 2-propanol/water solvent systems. FIGS. 11A and 11B show the relative analyte peak heights for pentachlorobenzene and fluoranthene plotted as a function of the effective Hildebrand solubility parameter (HSP) of the sample solution. The signal intensities are normalized to the signal obtained with a pure water matrix (HSP=48 MPa$^{\frac{1}{2}}$). Particularly, these plots show results of the following solvents:

| (Symbol) | FIG. 11A | (Symbol) | FIG. 11B |
|---|---|---|---|
| a | Pentachlorobenzene (ACN) | e | Fluoranthene (ACN) |
| b | Pentachlorobenzene (ACE) | f | Fluoranthene (ACE) |
| c | Pentachlorobenzene (MeOH) | g | Fluoranthene (MeOH) |
| d | Pentachlorobenzene (2-Prop) | h | Fluoranthene (2-Prop) |

For a given analyte, the signal or collection efficiency trends appear to be dependent on the solutions HSP. The absolute extent of the solvent effect, however, depends on the specific organic solvent present in the sample solution. For example, as illustrated in the relative fluoranthene response shown in FIG. 11B, maximum collection efficiency was observed for all of the solvent systems when the effective solution HSP was in the range of between about 42 and 46. The absolute value of the collection efficiency maxima follow the order acetonitrile > acetone > methanol > 2-propanol.

From the data presented on the effect of organic solvents in the sample solution, two major points may be gleaned. First, the RPM cell of the present invention is very effective at extracting the organic analytes of environmental interest from sample matrixes (solutions) which contain significant organic solvent content. This effect is unexpected, since one would always expect decreases in extraction efficiency relative to pure water as the organic nature of the sample solution is increased. These tests demonstrate that the collection efficiency can actually be enhanced in solutions which contain certain organic solvent content. Thus, an aqueous sample stream may be mixed with an organic solvent prior to contacting the RPM cell in order to enhance analyte collection and increase sensitivity.

Second, since the collection efficiency of the analytes is dependent on the sample solution HSP, sample streams may be modified with specific organic solvents in specific concentrations whereby the RPM collection may greatly favor specific analytes resulting in increased selectivity.

Having shown and described the preferred embodiment of the present invention, further adaptions of the apparatus and method for reversed permeation membrane extraction described herein can be accomplished by appropriate modifications by one of ordinary skill in the art without departing from the scope of the present invention. Many of the potential modifications and adjustments have been discussed herein, and others will be apparent to those skilled in the art. Accordingly, the scope of the present invention should be considered in terms of the following claims, and is understood not to be limited to the details of structure and operation shown and described in the specification and drawings.

We claim:

1. A reversed permeation membrane assembly for the collection of one or more compounds of interest from a sample solution, said membrane assembly comprising:
    a semi-permeable membrane of predetermined thickness and length, said membrane having an inner surface and an outer surface;
    a substantially rigid membrane support attached to said semi-permeable membrane adjacent said outer surface; and
    a non-porous, non-permeable barrier adjacent to said substantially rigid support and which contacts said outer surface of said membrane to prevent permeation of compounds beyond said outer surface of said membrane in use.

2. The membrane assembly of claim 1, wherein said semi-permeable membrane comprises a substantially tubular conformation through which sample solution may be passed.

3. The membrane assembly of claim 2, wherein said membrane support also comprises a substantially tubular member within which said semi-permeable membrane is mounted.

4. The membrane assembly of claim 3, wherein said membrane support comprises a pair of oppositely disposed ends, and further comprising a peripheral seal between said membrane and said tubular support at least adjacent said oppositely disposed ends.

5. The membrane assembly of claim 1, further comprising means for attaching said assembly directly to an analytical device such as a liquid chromatograph, gas chromatograph, flow injection analysis apparatus, or the like, for in-line analysis of one or more compounds collected with said membrane assembly.

6. The membrane assembly of claim 1, wherein said membrane support comprises a substantially tubular member within which said membrane is supported, and said membrane assembly comprises means for accommodating elevated pressures within said support member for use with analytical procedures requiring the same.

7. The membrane assembly of claim 1, wherein said membrane comprises a silicone polymer.

8. The membrane assembly of claim 7, wherein said membrane support comprises a fused silica tube having an inner diameter upon which said silicone membrane is mounted.

9. A method of collecting one or more compounds of interest from a sample solution, said method comprising the steps of:

providing a reversed permeation collection cell comprising a semi-permeable membrane of predetermined thickness and length, said membrane having an inner surface and an outer surface, a substantially rigid membrane support attached to said semi-permeable membrane adjacent said outer surface, and a non-porous, non-permeable barrier which contacts said outer surface of said membrane to prevent permeation of compounds beyond said outer surface of said membrane in use;

passing a volume of sample solution in contact with the inner surface of said membrane such that one or more compound of interest permeates into and is retained in said membrane;

flushing the portion of said sample solution which has not permeated into the membrane from said membrane;

passing a volume of extractant solution in contact with the inner surface of said membrane to extract one or more retained permeated compound from said membrane by desorbing said one or more retained permeated compound into said extractant solution by reversed permeation; and assaying the extracted one or more compound of interest.

10. The method of claim 9, further comprising the step of flushing said sample solution from said membrane cell after said one or more compound of interest has permeated into said membrane from said solution.

11. The method of claim 9, wherein said sample solution is brought into contact with said membrane as a flowing sample of predetermined volume, moving along said membrane within said collection cell.

12. The method of claim 9, wherein said sample solution is brought into contact with said membrane and held in contact with said membrane within said collection cell for a predetermined period of time to facilitate permeation of said one or more compound into said membrane.

13. The method of claim 9, wherein said sample solution is brought into contact with said membrane for compound collection at a first collection location, the collection cell in which one or more permeated compound of interest is retained is thereafter transported to a second separate location, and the step of passing the extractant solution in contact with said membrane is completed at said second location.

14. The method of claim 9, wherein said assay step comprises analysis of extracted compound by gas or liquid chromatography.

15. The method of claim 14, wherein said gas or liquid chromatography is completed on-line with the collection and extraction steps connection of said reversed permeation collection cell to a gas or liquid chromatograph.

16. The method of claim 15, wherein the steps of passing the sample solution in contact with the membrane, extracting permeated compound from said membrane, and assay of said extracted compound are completed successively and automatically by direct connection of said collection cell with a gas or liquid chromatograph.

17. The method of claim 9, wherein a flush step is completed after said sample solution is passed in contact with said membrane to remove any residual sample solution from said collection cell and prior to contact of the membrane with said extractant solution.

* * * * *